United States Patent [19]

Negrevergne

[11] 4,046,916
[45] Sept. 6, 1977

[54] N-(CARBOXYMETHOXY-BENZYLIDINE)-CARBOXY ANILINES AND PHARMACEUTICAL COMPOSITIONS THEREOF

[75] Inventor: Georges Negrevergne, Bordeaux, France

[73] Assignee: Societe Anonyme Cortial S.A., Paris, France

[21] Appl. No.: 529,464

[22] Filed: Dec. 4, 1974

Related U.S. Application Data

[62] Division of Ser. No. 327,236, Jan. 26, 1973, Pat. No. 3,947,587.

[30] Foreign Application Priority Data

Jan. 27, 1972 France .................................. 72.02644

[51] Int. Cl.$^2$ .......................................... C07C 101/66
[52] U.S. Cl. .............................. 424/319; 260/295 R; 260/296 R; 260/296 D; 260/343.6; 260/518 R; 260/518 A; 260/519; 260/558 A; 260/559 R; 260/566 R; 260/566 D; 424/263; 424/266; 424/285; 424/310; 424/324; 424/330
[58] Field of Search .......... 260/471 R, 566 R, 566 D, 260/518 R, 518 A, 519; 424/310, 319

[56] References Cited

U.S. PATENT DOCUMENTS

| | | | |
|---|---|---|---|
| 2,976,217 | 3/1961 | Kreps | 260/471 R X |
| 3,252,761 | 5/1966 | Jungreis | 260/519 X |
| 3,592,913 | 7/1971 | Fujinami et al. | 424/310 X |
| 3,674,844 | 7/1972 | Shen et al. | 260/471 R X |
| 3,842,120 | 10/1974 | Sprenger | 260/471 R |

FOREIGN PATENT DOCUMENTS

| | | | |
|---|---|---|---|
| 1,178,601 | 5/1959 | France | 260/566 R |
| 1,427,102 | 10/1966 | France | 260/566 R |
| 1,437,423 | 10/1966 | France | 260/471 R |

OTHER PUBLICATIONS

Reeves et al., JACS, 85 (1963) pp. 724-728.
Kaikaris, Chemical Abstracts, 64 (1966) 11097.

*Primary Examiner*—Richard L. Raymond
*Attorney, Agent, or Firm*—Brumbaugh, Graves, Donohue & Raymond

[57] ABSTRACT

Novel products having analgesic and antipyretic activity are provided having the formula:

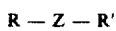

in which each of R and R', which may be the same or different, represents a phenyl or pyridyl radical which is optionally substituted by at least one substituent selected from a halogen atom, $-NO_2$, $-CONH_2-$, $-OC_2H_5$, $OCH_3$, $-CH_3$, $-COOC_2H_5$, $-COOCH_3$, $-COOH$ and $-OCH_2-COOH$ radical; Z represents a radical selected from $-CH=N-$ and $>CH-NH-$ in which the radical $>CH-$ of said amino group forms part of a heterocyclic structure of the formula:

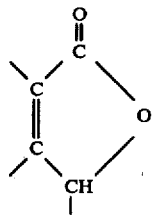

in which the two carbon atoms connected by a double bond form part of the radical R or R'. Specific compounds include 2-(2'-carboxamido-anilino)-o-phthalide and 2-(2' or 4'-ethoxy-anilino)-o-phthalide.

12 Claims, No Drawings

N-(CARBOXYMETHOXY-BENZYLIDINE)CARBOXY ANILINES AND PHARMACEUTICAL COMPOSITIONS THEREOF

This is a division of application Ser. No. 327,236, filed Jan. 26, 1973, now U.S. Pat. No. 3,947,587.

The present invention relates to new products obtained by reacting a primary amine and an aldehyde.

The products according to the invention are products of the formula:

in which each of R and R', which may be the same or different, represents a phenyl, which is preferred, or pyridyl radical, which can optionally be substituted by at least one substituent selected especially from a halogen atom, —NO₂, —CONH₂, —OC₂H₅, —OCH₃, —COOC₂H₅, —COOCH₃, —COOH and —OCH₂—COOH radicals, and Z is an imine diradical of formula —CH = N— or an amino diradical of formula >CH—NH— in which the radical >CH— of said amino radical forms part of a heterocyclic structure of the formula:

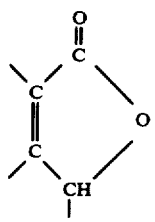

in which the two carbon atoms connected by a double bond form part of the radical R. R and R' typically represent a phenyl radical optionally substituted by —Cl, —COOH, —COOCH₃, —CONH₂, —CH₃ or —OC₂H₅.

The new products can be prepared, according to this invention, by a process which comprises heating under reflux substantially equimolar amounts of an aldehyde of the formula: R—CHO and of a primary amine of the formula: R'—NH₂ dissolved in a suitable solvent, such as ethanol or methyl ethyl ketone or a mixture of such solvents, and precipitating the product obtained by cooling.

The desired product can be recovered by, for example, filtration and purified by, for example, crystallisation from an alcohol e.g. ethyl alcohol or an aqueous alcoholic solution until a compound is obtained which has a definite and constant melting point.

When the aldehyde R—CHO does not carry a carboxylic acid group on a carbon adjacent to that carrying the aldehyde group, the condensation products obtained have an imine structure; these products can thus be represented by the general formula:

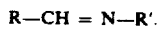

On the other hand, when the aldehyde R—CHO does carry a carboxylic acid group on a carbon adjacent to that carrying the aldehyde group, the condensation products obtained have a phthalide structure which can be represented by the following formula:

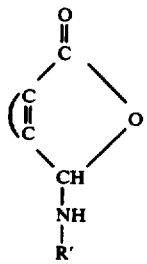

in which the ring

is the R ring. In other words the phenyl or pyridyl radical which R and R' represent can be divalent as well as monovalent.

The products of this invention possess useful anti-inflammatory, analgesic, hypothermal and antipyretic activity. Thus the present invention also provides pharmaceutical compositions containing an effective amount of at least one product of the present invention, together with an appropriate carrier or diluent. The products can be administered orally, rectally or percutaneously.

Taking account of their diverse pharmacological activities and their low toxicity, the compounds of the present invention can be used in human therapy, in inflammatory and algesic conditions, especially:

In rheumatology: chronic inflammatory rheumatism, degenerative rheumatism, abarticular diseases and gout, In functional re-training, In traumatology: sprains, tendinites, sore muscles and after-effects of fractures, and In dermato-phlebology: phlebites, periphlebites, varices and cellulitis.

They can be administered orally, rectally and percutaneously, in numerous pharamceutical forms such as tablets, dragees, gelatine-coated pills, capsules, suppositories, ointments and gels. Naturally, they can be combined with vehicles suited to these pharmaceutical forms.

The oral forms suitably contain 0.100 g to 1.500 g per unit dose, the suppositories 0.250 g to 1 g and the ointments and gels 5 to 10% by weight.

The average daily posology is 2 to 3 doses with oral administration, 1 to 2 doses with rectal administration and 2 to 3 applications with percutaneous administration.

Naturally, the duration of the treatment depends on the condition being treated.

The following Examples further illustrate the present invention.

EXAMPLE 1

18 g of p-formyl-phenoxyacetic acid and 13.7 g of anthranilic acid are heated in approximately 150 ml of methyl ethyl ketone under reflux for 2 hours; after precipitation and recrystallisation from aqueous ethanol, 24 g of condensation product are obtained, having a melting point of 200° C; the yield is 80%.

EXAMPLE 2

15 g of phthalaldehydic acid and 13.7 g of o-ethoxy-aniline in approximately 180 ml of acetone are heated under reflux for 2 hours. After precipitation and recrystallisation, 19 g of 3-(o-ethoxyaniline)-phthalide are obtained having a melting point of 115° C; the yield is 70%.

EXAMPLE 3

13.7 g of anthranilic acid and 10.7 g of isonicotinic aldehyde in approximately 150 ml of methyl ethyl ketone are heated under reflux for 2 hours; after precipitation and recrystallisation from aqueous ethanol, 18 g of N-(4-pyridyl-methylene)-anthranilic acid are obtained having a melting point of 120° C; the yield is 80%.

EXAMPLE 4

16.2 g of 2,6-dichloro-aniline and 15 g of o-phthalic acid aldehyde, dissolved in 120 ml of diethyl ketone, are heated under reflux for 4 hours. After evaporation of the solvent and recrystallisation, 21 g (70% yield) of 2-(2',6-dichloro-anilino)-phthalide are obtained having a melting point of 150° C.

The majority of the compounds are crystalline powders, the melting point of which varies from 120° to 260° C; the following products can be prepared according to an analogous process:

| | | |
|---|---|---|
| N-salicylidene-2,4,5-trichloro-aniline | M.p. | 136° C. |
| 3-N-(2'-methoxybenzylidene)carboxy-aniline | M.p. | 260° C. |
| 2-N-(2'-carboxymethoxy-benzylidene)carboxy-aniline | M.p. | 180° C. |
| 3-N-(2'-carboxymethoxy-benzylidene)carboxy-aniline | M.p. | 145° C. |
| 4-N-(2'-carboxymethoxy-benzylidene)carboxy-aniline | M.p. | 254° C. |
| 2-N-(4'-carboxymethoxy-benzylidene)carboxy-aniline | M.p. | 200° C. |
| 3-N-(4'-carboxymethoxy-benzylidene)carboxy-aniline | M.p. | 240° C. |
| 4-N-(4'-carboxymethoxy-benzylidene)carboxy-aniline | M.p. | 260° C. |
| 3-N-(picolinylidene)carboxy-aniline | M.p. | 207° C. |
| N-(picolinylidene)para-carbethoxy-aniline | M.p. | 130° C. |
| 3-N-(nicotinylidene)hydroxy-aniline | M.p. | 260° C. |
| 2-N-(nicotinylidene)carboxy-aniline | M.p. | 110° C. |
| 2-(3'-hydroxy-anilino)-o-phthalide | M.p. | 148° C. |
| 2-(2'-carboxy-anilino)-o-phthalide | M.p. | 260° C. |
| 2-(2'-carboxyamido-anilino)-o-phthalide | M.p. | 225° C. |
| 2-(4'-carboxy-anilino)-o-phthalide | M.p. | >260° C. |
| 2-(3'-trifluoro-anilino)-o-phthalide | M.p. | 144° C. |
| 2-(2',4'-dichloro-anilino)-phthalide | M.p. | 148° C. |
| 2-(2',6'-dichloro-anilino)-phthalide | M.p. | 150° C. |
| 2-(2',6'-dimethyl-anilino)-phthalide | M.p. | 132° C. |
| 2-(2',4'-dimethyl-anilino)-phthalide | M.p. | 156° C. |
| 2-(2',4',6'-trichloro-anilino)-o-phthalide | M.p. | 58° C. |
| 2-(2'-carbomethoxy-anilino)-o-phthalide | M.p. | 220° C. |
| 2-(2'-ethoxy-anilino)-o-phthalide | M.p. | 115° C. |
| 2-(3'-ethoxy-anilino)-o-phthalide | M.p. | 118° C. |
| 2-(4'-ethoxy-anilino)-o-phthalide | M.p. | 179° C. |
| 2-(4'-carboxy-3'-hydroxy-anilino)-o-phthalide | M.p. | 68° C. |
| 2-(2'-methyl-3'-chloro-anilino)-o-phthalide | M.p. | 186° C. |
| 2-(2'-methyl-4'-chloro-anilino)-o-phthalide | M.p. | 196° C. |
| 2-(2'-methyl-5'-chloro-anilino)-o-phthalide | M.p. | 168° C. |
| 2-(2'-methyl-6'-chloro-anilino)-o-phthalide | M.p. | 68° C. |
| 2-(4'-methyl-3'-chloro-anilino)-o-phthalide | M.p. | 191° C. |
| bis-(2-o-phthalido)-meta-phenylene-diamine | M.p. | 260° C. |
| 2-(2'-chloro-4'-nitro-anilino)-o-phthalide | M.p. | 204° C. |

These products are insoluble in water and carbon tetrachloride; they are sparingly soluble in ethyl alcohol and chloroform and sparingly soluble in acetone and tetrahydrofurane, and soluble in pyridine.

The insolubility of these products in carbon tetrachloride makes it impossible to investigate them by N.M.R. On the other hand, microanalytical determinations gave the expected results. Moreover, the I.R. spectra of the products dispersed in nujol or mixed with potassium bromide show (where expected) the absorption characteristic of the aromatic imine group at 6.15 μ and of the lactone carboxyl group of phthalides at 5.7 μ.

The compounds thus produced showed considerable anti-inflammatory, analgesic and anti-pyretic activities.

Pharmacological and toxicological investigations gave the following results:

The pharmacological investigation was directed towards the anti-inflammatory, analgesic and anti-pyretic action, a few Examples of which follow by way of illustration.

EXAMPLE 5

Investigation of anti-inflammatory activity

Rats which received a phlogogenic substance such as a solution of formaldehyde or carragenine in the pads of their feet, and to which 250 mg/kg of the products according to the invention were administered orally at the same time, had their oedema markedly inhibited relative to those which had not ingested the product. The same result was obtained in the case of rats which had received 400 mg/kg, administered orally, of the product according to the invention 30 minutes before plantar injection of serotonine.

The compounds of the present invention can also act when the oedema is developed. Thus, 6 hours after the injection of kaolin under the same conditions as above, rats which had received 400 mg/kg of product according to the invention, administered orally, also had their oedema considerably reduced.

Finally, it was found that the products according to the invention possess very valuable antiinflammatory activity at smaller repeated doses. Thus rats into the sides of which cotton pellets were introduced, via the skin of the back, thus causing the formation of granulomas, and which had received 100 mg/kg of product according to the invention for 10 consecutive days, had their granulomatous tissue considerably reduced relative to untreated control rats.

In this investigation of the anti-inflammatory activity, some of the compounds proved to be particularly effective, as is shown in the Table below.

TABLE

| Anti-inflammatory activity | | | |
|---|---|---|---|
| Products according to the invention | Dose administered | Injection of carragenine | Injection of serotonine |
| 3-N-(4'-carboxymethoxy-benzylidene-carboxy-aniline | 400 mg/kg | | X |
| N-salicylidene-2,4,5-trichloro-aniline | 250 mg/kg | X | |
| 2-(4'-ethoxy-anilino)-o-phthalide | 250 mg/kg | X | |
| 2-N-(4'-carboxymethoxy-benzylidene)-carboxy-aniline | 250 mg/kg | X | |
| 2-(2',6'-dichloro-anilino)-phthalide | 100 mg/kg 10 consecutive days | | |

| Products according to the invention | Kaolin | Cotton pellets | Decrease in oedema |
|---|---|---|---|
| 3-N-(4'-carboxymethoxy-benzylidene)-carboxy-aniline | | | 38.2% |
| N-salicyidene-2,4,5-trichloro-aniline | X | | 20.6% (carragenine) 15% (kaolin) |
| 2-(4'-ethoxy-anilino)-o-phthalide | | | 55% |
| 2-N-(4'-carboxymethoxy-benzylidene)-carboxy- | | | 34% |

TABLE-continued

| Anti-inflammatory activity | | |
|---|---|---|
| aniline 2-(2',6'-dichloro-anilino)-phthalide | X | 34% (pellets) |

EXAMPLE 6

Investigation of analgesic activity

A batch of mice weighing approximately 20 g, which were sensitive to phenyl-p-benzoquinone, that is to say mice in which phenyl-p-benzoquinone, when administered intraperitoneally, causes a very characteristic twist syndrome, was selected.

Half of these mice had previously received 250 mg/kg of product according to the invention, administered orally. The number of twists made by the mice after injection was counted and a marked decrease in this number was observed in the case of the treated mice.

Certain compounds proved to be particularly interesting analgesics, as is shown in the following Table:

| Analgesic activity in mice which had reacted to an injection of phenyl-p-benzoquinone. | | |
|---|---|---|
| Products according to the invention | Dose administered | Percentage activity |
| 2-(2'-carboxamido-anilino)-o-phthalide | 250 mg/kg | 70% |
| 2-(2'-ethoxy-anilino)-o-phthalide | 250 mg/kg | 70% |
| 2-(2',4'-dimethyl-anilino)-phthalide | 250 mg/kg | 50% |

EXAMPLE 7

Anti-pyretic activity

The products according to the invention proved to be anti-pyretic agents, without however changing the body temperature of the animals. Thus, for example, mice which were known to possess a normal body temperature and which had received 250 mg/kg of product according to the invention, did not have their body temperature changed during the 24 hours following ingestion.

On the other hand, mice which received 10 ml/kg of pyrogenic solution, administered subcutaneously, and then, 4 hours after, ingested 250 mg/kg of the product according to the invention, returned to a normal temperature very rapidly.

Determination of the LD 50 demonstrated the low degree of damage of these compounds with respect to mice. The great majority of the compounds according to the invention have an LD 50, after a period of 24 hours, greater than 2 g/kg. Several have an LD 50 greater than 5 g/kg.

I claim:
1. The product 2-N-(4'-carboxymethoxy-benzylidene)-carboxy-aniline.
2. The product 3-N-(4'-carboxymethoxy-benzylidene)-carboxy-aniline.
3. The product 2-N-(2'-carboxymethoxy-benzylidene)-carboxy-aniline.
4. The product 3-N-(2'-carboxymethoxy-benzylidene)-carboxy-aniline.
5. The product 4-N-(2'-carboxymethoxy-benzylidene)-carboxy-aniline.
6. The product 4-N-(4'-carboxymethoxy-benzylidene)-carboxy-aniline.
7. A pharmaceutical composition having analgesic and anti-pyretic activity which comprises as the active ingredient a therapeutically effective amount of the product of claim 1.
8. A pharmaceutical composition having analgesic and anti-pyretic activity which comprises as the active ingredient a therapeutically effective amount of the product of claim 2.
9. A pharmaceutical composition having analgesic and anti-pyretic activity which comprises as the active ingredient a therapeutically effective amount of the product of claim 3.
10. A pharmaceutical composition having analgesic and anti-pyretic activity which comprises as the active ingredient a therapeutically effective amount of the product of claim 4.
11. A pharamceutical composition having analgesic and anti-pyretic activity which comprises as the active ingredient a therapeutically effective amount of the product of claim 5.
12. A pharmaceutical composition having analgesic and anti-pyretic activity which comprises as the active ingredient a therapeutically effective amount of the product of claim 6.

* * * * *